(12) United States Patent
Biffi Gentili et al.

(10) Patent No.: US 7,889,077 B2
(45) Date of Patent: Feb. 15, 2011

(54) PORTABLE DEVICE FOR THE DETECTION OF CONCEALED OBJECTS

(75) Inventors: Guido Biffi Gentili, Florence (IT); Filippo Bonifacio, Florence (IT); Paolo Moretti, Fiesole (IT); Rinaldo Rinaldi, Arezzo (IT)

(73) Assignee: Saima Sicurezza SpA, Arezzo (IT)

( * ) Notice: Subject to any disclaimer, the term of this patent is extended or adjusted under 35 U.S.C. 154(b) by 126 days.

(21) Appl. No.: 11/741,512

(22) Filed: Apr. 27, 2007

(65) Prior Publication Data

US 2008/0111536 A1    May 15, 2008

(30) Foreign Application Priority Data

Apr. 28, 2006  (IT) .............................. FI2006A0098

(51) Int. Cl.
*G08B 13/14* (2006.01)
*G08B 23/00* (2006.01)
*G01R 27/04* (2006.01)
*G01R 27/32* (2006.01)

(52) U.S. Cl. .................. 340/568.1; 340/573.1; 324/637

(58) Field of Classification Search ............. 340/568.1, 340/500–506, 631, 532, 539.11, 539.22, 340/539.26, 539.32, 539.23, 540, 568.2, 340/571, 572.1, 686.1, 686.6, 693.5, 693.6, 340/3.1, 825.36, 573.1; 324/637–639, 641, 324/642, 644–646
See application file for complete search history.

(56) References Cited

U.S. PATENT DOCUMENTS

| | | | | |
|---|---|---|---|---|
| 4,975,968 A * | 12/1990 | Yukl | ............................ | 382/100 |
| 5,073,782 A * | 12/1991 | Huguenin et al. | ............ | 342/179 |
| 6,057,761 A * | 5/2000 | Yukl | ........................ | 340/568.1 |
| 6,150,810 A * | 11/2000 | Roybal | ......................... | 324/244 |
| 6,480,141 B1 * | 11/2002 | Toth et al. | ...................... | 342/22 |
| 7,015,817 B2 * | 3/2006 | Copley et al. | ............. | 340/573.4 |
| 7,051,817 B2 * | 5/2006 | Shaposhnikov et al. | ...... | 166/372 |
| 7,417,440 B2 * | 8/2008 | Peschmann et al. | .......... | 324/637 |

* cited by examiner

*Primary Examiner*—Jennifer Mehmood
(74) *Attorney, Agent, or Firm*—Knobbe Martens Olson & Bear LLP

(57) ABSTRACT

The object of the present invention is a device for the detection of concealed objects which exploits a transceiving system of the microwave type.

2 Claims, 2 Drawing Sheets

PORTABLE DEVICE FOR THE DETECTION OF CONCEALED OBJECTS

CROSS REFERENCE TO RELATED APPLICATIONS

This application claims the benefit of Italian Patent FI2006A000098, filed on Apr. 28, 2006, the disclosure of which is incorporated herein in its entirety by reference.

FIELD OF THE INVENTION

The present invention relates to the field of devices for detecting concealed objects.

STATE OF THE ART

In the field of the apparatuses and devices for the detection of concealed objects, the so-called metal detectors which are installed in large number to monitor the sensitive entrances to airports, museums, banks, law courts, etc. have prominent importance. Said metal detectors signal the presence of metallic objects, worn or concealed elsewhere, and may be either fixed (safety doors at airport boarding gates) or portable (the detectors used by guards in proximity of the airport boarding gates) but are not capable of detecting non-metallic objects, such as weapons formed by plastic or ceramic materials or explosives.

Other types of devices for the detection of concealed objects are capable of also signalling the presence of non-metallic objects. Said devices may be of various types according to the phenomenon exploited for performing the detection. Therefore, there are x-ray, magnetic resonance, acoustic and infrared detectors, millimetric wave detectors, frequency modulation continuous wave (FMCW) detectors, radar detectors, microwave detectors and each of them exploits a certain physical or electromagnetic phenomenon to determine the "abnormality" represented by the object concealed under the clothes or inside casings, bags, luggage, etc. Each of the concealed object detectors mentioned above displays advantages and disadvantages related to the usual evaluation parameters of these devices which are precision, efficiency, impact on controlled individuals, ease of use, cost.

Considering and evaluating the parameters above, microwave detectors are certainly among the best detectors even though they display, as all the others, strengths and drawbacks. Specifically, microwave detectors of the dielectrometric type are an excellent accommodation between performances, costs and simplicity of use, but are generally made as fixed devices, often in the form of gates—through which the controlled person is made to pass, following certain modalities. The device object of the present invention is a concealed object detector of the microwave type, of small dimensions so that it may be used in apparatuses of the portable type.

SUMMARY OF THE INVENTION

The object of the present invention is a device for the detection of concealed objects which exploits a transceiving system of the microwave type, of reduced dimensions so that it may be used in apparatuses of the portable type.

DETAILED DESCRIPTION OF THE INVENTION

The device according to the present invention is a microwave technology based concealed object detector which allows easy integration in small dimensions and low risk for controlled individuals. The microwaves are exploited to measure possible dielectric discontinuities existing in contact with the controlled individual's body, dielectric discontinuities which may be indicative of the presence of a foreign object.

The operating principle of the invention, however, is independent from the operating frequency and may theoretically be successfully used at operating frequencies from the UHF to the microwave bands, i.e. from 300 MHz to 100 GHz. Within this broad frequency spectrum, some bands appeared of specific interest for the practical implementation of the invention. Specifically: the ISM band from 2.4 to 2.483 GHz, the ISM band from 5.725 to 5.875 and the band from 14 GHz to 30 GHz.

The features which make the first two frequency bands particularly interesting are essentially the low cost, the easy availability of the components and the possibility of making directive radiating elements with relatively contained dimensions. In the case of the band from 14 GHz to 30 GHz, instead, the response of the human body is particularly favourable for the objects of the present invention because it displays a reflection coefficient nearly solely linked to the skin layer and therefore virtually independent from the fabrics and the lack of homogeneousness under the skin (bones, muscles, etc.) which constitute elements of disturbance for the measurement.

The operation of the device according to the present invention is further independent from the technology exploited for making the radiating element, although two specific types of antennas have been considered most suitable for making the device according to the present invention: the planar antennas which allow the relatively simple making of also rather complex structures and arrays and further allow an easy integration with the circuits to which said antennas are connected and the aperture antennas which have superior polarisation purity features although they are most costly and cumbersome.

Figure 1:
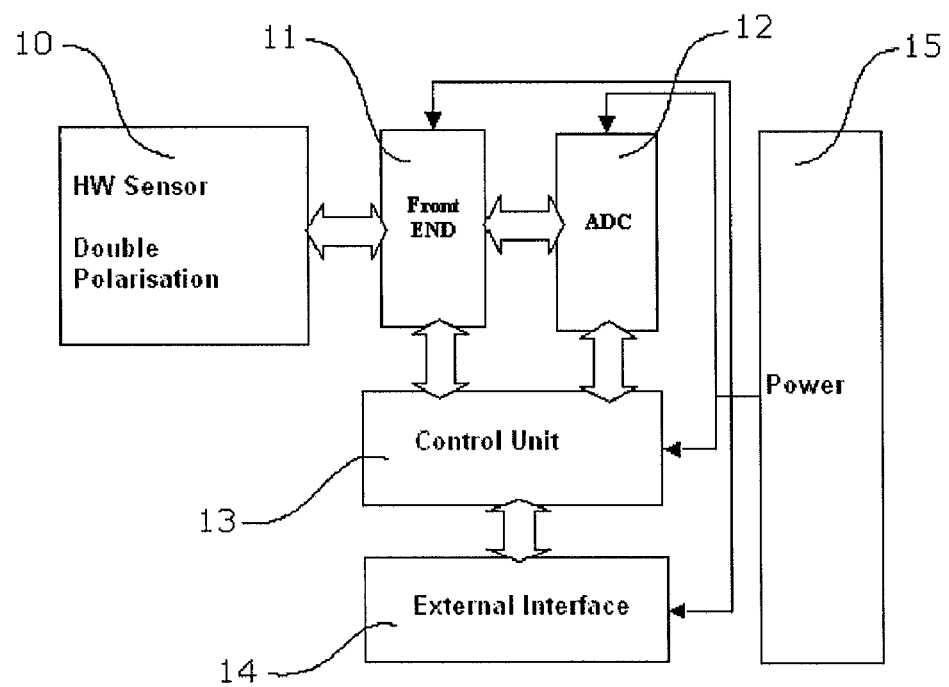
FIG. 1 is a general block diagram of the device according to the present invention.

With reference to FIG. 1, the block diagram of the device according to the present invention comprises:

a microwave sensor module 10 adapted to emit and receive electromagnetic radiation, preferably microwave radiation, from and to the target. Said microwave sensor module 10 is characterised in that it transmits and receives an electromagnetic signal according to two separate polarisations spatially oriented at 90 degrees one with respect to the other.

a so-called front end module 11 adapted to generate and acquire the microwave signal corresponding to said electromagnetic radiation. Preferably said front end module 11 further displays control signal inputs—preferably digital—which allow the management by a logical processing and control unit 13 and outputs related to control signals, preferably of analogue type.

A conditioning and analogue digital conversion module 12, adapted to perform a first analogue processing of the signals from front end module 11 and a subsequent digital conversion step of the processed signals. Examples of analogue processing may be filtering, amplifications, offset additions. Conditioning and analogue digital conversion module 12 works in connection with the subsequent logical processing and control unit 13 sending data in digital format and receiving settings and control signals therefrom.

A logical processing and control unit 13 adapted to provide the possible alarm following the detection of the presence of a concealed object and of managing the data pertaining to calibration, acquisition mode and response decision criteria. This block will preferably comprise at least one processor associated to at least one memory unit. This block will display logical interconnections with front end block 11, conditioning and conversion block 12 and user interface block 14 with which it exchanges commands, data and settings.

A user interface 14 adapted to communicate the results of the measurement performed by means of appropriate signalling means (acoustic indicators, displays, etc.) to the operator and to receive the operative commands (start measurement, stop measurement, etc.) therefrom by means of appropriate data entry means comprising, for example, an alphanumeric keypad. Furthermore, said user interface preferably comprises appropriate interface means with external control devices such as for example a personal computer with which it is possible to exchange data or receive commands or settings.

A power supply module 15 adapted to allow the stand-alone operation of the device will thus preferably comprise possibly rechargeable batteries, recharging circuits of said rechargeable batteries and indicators of their charge state.

Figure 2:
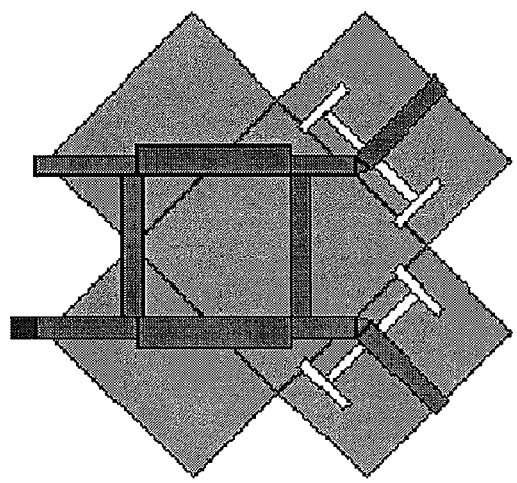
FIG. 2 is the transceiving element used in a first preferred embodiment of the present invention.

The operation of the device according to the invention is as follows: the transceiving element exploits a double polarisation so as to generate two microwave signals spatially polarised at 90 degrees. In a first preferred embodiment of the present invention, said transceiving element is made as shown in the drawing in FIG. 2. It comprises two antennas having the same centre of symmetry and having a reciprocal spatial phase of 90 degrees. Each antenna works both as transmitter and as receiver for its polarisation. The described architecture, characterised by a centre of symmetry in common to both antennas, allows the detection to be particularly immune from the related inclination between sensor and target.

If said two antennas are powered by means of a 90° degree electric hybrid, a circular polarisation is produced and it is demonstrated that a reflection coefficient expressed by the following relation is obtained at the feeding port:

$$S_{11} = (\Gamma_v - \Gamma_h)$$

In other words at the feeding port of the hybrid there is a reflection coefficient equal to the vectorial difference of the horizontal and vertical reflection coefficients and therefore there is, in fact, a signal proportional to the lack of homogeneousness of the background investigated by the two microwave signals which may be processed to detect the presence of the concealed object which caused the abovementioned lack of homogeneousness.

The measurement procedure performed by the device according to the present invention contemplates the following steps:
a) Scanning the object of the measurement by means of preferably microwave electromagnetic signal. Said scanning occurs by means of generating, transmitting, receiving and detecting signals in both polarisations. The scanning steps may be performed according to different modalities: the transmission of the signals in two different polarisations may occur at the same time or not. Techniques such as dislocation between the polarisations (circular polarisation) or frequency separation may be used. This step ends with the production of analogue signals containing information related to the measurement in progress. Examples of signals output by the front end during this step are: amplitude of the signals in the two polarisations, their phase, the relation between their amplitudes, the reciprocal phase between the signals in different polarisations, the vectorial difference between the signals related to the two polarisations, etc.
b) Analogue and conversion conditioning of analogue data in digital format.
c) Processing. A series of logical and mathematical operations are performed on the data mentioned in the previous step, said operations being aimed at putting the device in condition to univocally and precisely deal with the following decision-making step.
d) Decision-making. Condition corresponding to the obtained data is established and appropriate signals are sent, by means of appropriate devices—typically of the optical or acoustic type—by means of which the operator is informed about the condition related to the performed measurement. Note that the responses given by the system may go beyond the simple "Alarm on"-"Alarm off". For example, the system may be set up so as to further contemplate the measurement error indication if the measurement is preformed in non-optimal conditions (e.g. too far from the target).

Figure 3:
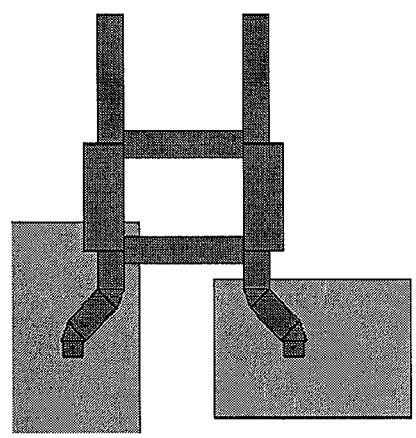
FIG. 3 is the double antenna used in a second preferred embodiment of the present invention.

In a second preferred embodiment, shown in FIG. 3, the microwave sensor element is made with two ninety degree polarising radiating elements having different centres of symmetry.

Figure 4:
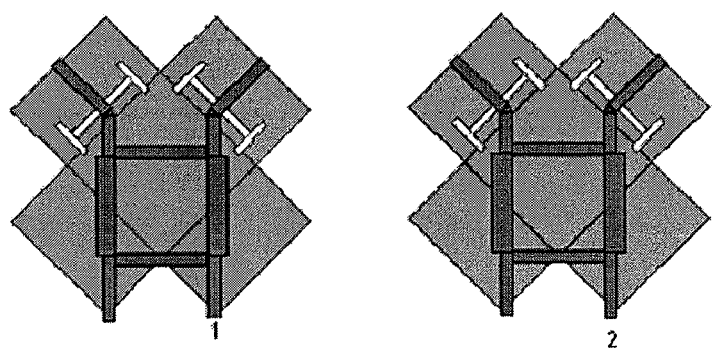
FIG. 4 is the double antenna used in a third preferred embodiment of the present invention.

In a third preferred embodiment of the present invention, the transceiving element of the device according to the present invention consists of a double antenna as shown in FIG. 4 characterised by a split between the transmitting and the receiving elements.

The cross antenna is thus split into two separate structures so that the concerned parameter to be measured is in this case transmission coefficient S21 which is proportional to the lack of homogeneousness of the reflecting background if a hidden object is present, instead of a reflection coefficient as above.

Figure 5:
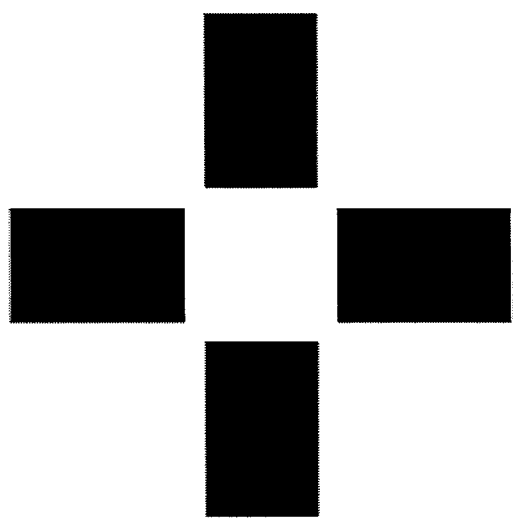
FIG. 5 is the four-element antenna used in a further preferred embodiment of the present invention.

In a further preferred embodiment of the present invention, the double antenna is made by spatially splitting the single antennas in the way shown in FIG. 5. In this case, four antennas are used, two of which are in vertical polarisation (Tx and Rx) and two in horizontal polarisation (Tx and Rx). Said four antennas are at the four vertexes of a square and those with the same polarisation are at opposite vertexes.

The polarisation, i.e. the orientation of the electrical field of each antenna, is parallel to the diagonal of the square related to the vertex where each antenna is located.

In this case, the lack of homogeneousness is measured by measuring transmission coefficients S31 and S42.

In a practical embodiment of said preferred embodiment of the device according to the present invention, the following constructive contrivances and the following working parameters were adopted:

Each of the used antennas consists of a planar array of 4 patches powered in phase in order to increase there directivity thereof.

Inclination of each radiating element so that the axes of all the antennas meet at approximately 20 cm of height.

Symmetric architecture of the front end with a single generator switchable between the two transmitting elements and a single logarithmic detector of switchable amplitude on the two receiving elements.

Insertion of radio-absorbing material in the middle of the sensor between the four antennas so as to attenuate multiple reflections and direct couplings.

Optimal working distance of approximately 10 cm.

Possibility of performing measurements on several frequencies—between 5.6 and 5.9 GHz—and possibility of processing data related to measurements at different frequencies as a whole.

Interfaceability with an external personal computer by means of a dedicated software which allows the programming of the main parameters and the display of the measurements in real time.

Acoustic alarm signal.

Powered by batteries of the rechargeable type.

In this embodiment, step a) of the procedure described above is performed according to the following steps:

I. Generating a microwave signal and transmitting this to the vertical polarisation transmitter.

II. Connecting the detector to the vertical receiving element and transmitting the analogue signal related to this measurement to the conditioning and conversion network.

III. Generating a microwave signal and transmitting this to the horizontal polarisation transmitter.

IV. Connecting the detector to the horizontal receiving element and transmitting the analogue signal related to this measurement to the conditioning and conversion network.

In this case, said analogue signals are proportional to the amplitude to the transmission coefficients of the vertical and horizontal transceived signals.

In a further practical implementation of said preferred embodiment of the device according to the present invention the following constructive contrivances and the following working parameters were adopted:

Microwave sensor of the planar type in which each antenna consists of a patch with slot feeding.

Front end architecture comprising two generation modules and two receivers. Each of the transmission antennas is directly connected to its generator and each of the reception antennas is directly connected to its receiver.

Possibility of performing measurements on several frequencies, in the 2.4-2.5 GHz range, and possibility of processing data related to measurements performed at different frequencies as a whole.

Working distance from the target of approximately 6 cm.

Interfaceability with an external personal computer by means of a dedicated software which allows the programming of the main parameters thereof and the display of the measurements in real time.

Acoustic alarm signal.

Powered by batteries of the rechargeable type.

Also in this case, said analogue signals are proportional to the amplitude of the transmission coefficients of the vertical and horizontal transceiver signals.

This second practical embodiment works in the close field range considering that the working distance is approximately 6 cm and therefore lower than the wavelength which is approximately 12.5 cm at working frequencies.

The invention claimed is:

1. A method of detecting concealed objects, the method comprising:
   scanning a target with microwave electromagnetic radiation;
   receiving a reflected signal from the target, the reflected signal corresponding to the microwave electromagnetic radiation;
   conditioning and converting analog data related to the received signal to a digital data format;
   processing the digital data;
   determining a condition corresponding to the digital data;
   generating a signal for an operator indicating the condition,
   wherein scanning the target comprises:
      generating the electromagnetic radiation;
      transmitting the electromagnetic radiation to the target with a vertical polarization transmitter;
      connecting a detector to a vertical receiving element;
      generating a signal based on radiation reflected from the target in response to the transmitted electromagnetic radiation;
      transmitting the signal to a signal conditioning and conversion module;
      generating additional electromagnetic radiation;
      transmitting the additional electromagnetic radiation to the target with a horizontal polarization transmitter;
      connecting the detector to the horizontal receiving element;
      generating an additional signal based on radiation reflected from the target in response to the transmitted additional electromagnetic radiation;
      transmitting the additional signal to the signal conditioning and conversion module.

2. The method according to claim 1, further comprising at least one of:
   determining amplitudes of the signal and the additional signal;;
   comparing phase between the signal and the additional signal;
   comparing amplitudes of the signal and the additional signal;
   determining a reciprocal phase between the signal and the additional signal; and
   determining a vectorial difference between the signal and the additional signal.

* * * * *